United States Patent
Lombardo et al.

(10) Patent No.: US 10,952,719 B2
(45) Date of Patent: Mar. 23, 2021

(54) KNOTLESS SUTURE ANCHOR CONSTRUCT

(71) Applicant: CONMED CORPORATION, Utica, NY (US)

(72) Inventors: Giuseppe Lombardo, New Port Richey, FL (US); Adrian Bosworth, Bradenton, FL (US)

(73) Assignee: CONMED CORPORATION, Utica, NY (US)

( * ) Notice: Subject to any disclaimer, the term of this patent is extended or adjusted under 35 U.S.C. 154(b) by 20 days.

(21) Appl. No.: 16/373,941

(22) Filed: Apr. 3, 2019

(65) Prior Publication Data
US 2019/0307441 A1 Oct. 10, 2019

Related U.S. Application Data

(60) Provisional application No. 62/652,968, filed on Apr. 5, 2018.

(51) Int. Cl.
*A61B 17/04* (2006.01)
(52) U.S. Cl.
CPC .. *A61B 17/0401* (2013.01); *A61B 2017/0459* (2013.01)
(58) Field of Classification Search
CPC .......... A61B 17/0401; A61B 17/06166; A61B 17/17; A61B 2017/404; A61B 2017/0403–0409; A61B 2017/042; A61B 2017/0464; A61B 2017/06185; A61B 2017/0459; A61F 2002/0852; A61F 2/0811
See application file for complete search history.

(56) References Cited

U.S. PATENT DOCUMENTS

| | | | | |
|---|---|---|---|---|
| 2010/0016892 | A1* | 1/2010 | Kaiser | A61B 17/0401 606/232 |
| 2013/0296934 | A1* | 11/2013 | Sengun | A61B 17/04 606/232 |
| 2014/0277133 | A1* | 9/2014 | Foerster | A61B 17/0401 606/232 |
| 2016/0157851 | A1* | 6/2016 | Spenciner | A61F 2/0811 606/232 |
| 2016/0270777 | A1* | 9/2016 | Miller | A61B 17/0401 |

* cited by examiner

*Primary Examiner* — George J Ulsh
*Assistant Examiner* — Andrew P. Restaino
(74) *Attorney, Agent, or Firm* — Bond, Schoeneck & King, PLLC; Frederick J. M. Price

(57) ABSTRACT

A knotless suture anchor construct for securing a tissue in a desired position relative to a bone hole. The construct includes an anchor body extending between first and second ends and having first and second sides. The construct also includes a filament having a first end and a second end. The filament is woven through a plurality of passing locations along the anchor body such that the first end of the filament extends from the first end of the anchor body and the second end of the filament extends from the second end of the anchor body. The construct additionally includes a first loop in the filament between a first adjacent pair of the plurality of passing locations and a second loop in the filament between a second adjacent pair of the plurality of passing locations. In a pre-deployment configuration, the second loop extends through the first loop.

21 Claims, 6 Drawing Sheets

KNOTLESS SUTURE ANCHOR CONSTRUCT

CROSS-REFERENCE TO RELATED APPLICATIONS

This application claims priority to U.S. Provisional Patent Application Ser. No. 62/652,968, filed on Apr. 5, 2018 and entitled "Knotless Instability Suture Anchor Construct and System," the entirety of which is incorporated herein by reference.

BACKGROUND OF THE INVENTION

1. Field of the Invention

The present invention is directed generally to suture anchors and, more particularly, to a knotless suture anchor construct for securing a tissue in a desired position relative to a bone hole.

2. Description of Related Art

Suture anchors are commonly used to repair soft tissue to bone in surgical procedures. Typically, suture anchors are inserted into a pre-formed hole and then accompanying sutures are passed through the tissue to be repaired. In many cases, a sliding knot is tied thereby allowing better tissue tensioning control and the surgeon can manipulate the sliding knot to bring the tissue in apposition to bone. In doing so, the tissue is naturally brought back to the point of origin of the suture and comes to rest directly over the pilot hole. To secure the sliding knot, the surgeon can tie one or more alternating half-hitch knots to complete the procedure. The act of tying a knot presents several challenges to the surgeon especially when tying them arthroscopically. Furthermore, in some cases, knots have been implicated as the source of post-operative pain caused by irritation from the knot stack.

Various types of suture anchors have been developed which are configured to fasten a suture in place without requiring the surgeon to tie a knot. Some designs capture the suture between two anchor components while others utilize an interference fit between the anchor and the bone tunnel. Many designs using these methods of fixation require the driver to be engaged with the anchor while tensioning the suture to bring the tissue into apposition with the bone. Since the driver is still engaged in the pilot hole, it prevents the tissue from being able to be tensioned so that it directly over the pilot hole (suture origin), thus giving a less than ideal tissue position and encumbering the adjustment of suture tension.

Others have addressed the problem of tissue position by the implementation of an adjustable loop which is formed around the tissue to be repaired. In this instance, the anchor is installed in bone and the driver is removed. One limb of the suture is free and passed through the tissue then into a loading filament which passes it back through the suture limb, creating a one-way loop. This requires the standing end of the suture to remain fixed so that it acts as a finger trap when the loop is tensioned, thereby preventing loop loosening. This method also requires a long length of suture to pass through or around the tissue before the loop is reduced, which can cause tissue damage by abrasion. Furthermore, the fixed end must reside deep in the hole and must not migrate or tensioning will be limited. Lastly, the aforementioned devices are comprised of a rigid material which can damage tissue if it pulls out of the hole during healing.

Therefore, there is a need for a simple to use suture anchor comprised of soft material which secures suture without the need to tie a knot and which facilitates the ability to adjust, maintain, and position tissue in desired location over the pilot hole during anchor installation and minimizes tissue abrasion during tensioning.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

The present invention is directed to a knotless suture anchor construct that is optimal for securing a tissue in a desired position relative to a bone hole. According to one aspect, the knotless suture anchor construct includes an anchor body extending between a first end and a second end. The anchor body has a first side and a second side. The knotless suture anchor construct also includes a filament having a first end and a second end. The filament is woven through a plurality of passing locations along the anchor body such that the first end of the filament extends from the first end of the anchor body and the second end of the filament extends from the second end of the anchor body. The knotless suture anchor construct additionally includes a first loop in the filament between a first adjacent pair of the plurality of passing locations and a second loop in the filament between a second adjacent pair of the plurality of passing locations. In a pre-deployment configuration, the second loop extends through the first loop.

According to another aspect, the knotless suture anchor construct includes an anchor body extending between a first end and a second end. The anchor body has a first side and a second side. The knotless suture anchor construct also includes a filament having a first end and a second end. The filament is woven through a plurality of passing locations along the anchor body such that the first end of the filament extends from the first end of the anchor body and the second end of the filament extends from the second end of the anchor body. The knotless suture anchor construct additionally includes a first passing portion in the filament between a first adjacent pair of the plurality of passing locations and a second passing portion in the filament between a second adjacent pair of the plurality of passing locations. In a pre-deployment configuration, the first passing portion is pulled to form a first loop and the second passing portion is pulled to form a second loop, and the second loop extends through the first loop.

According to another aspect, the present invention includes a method for securing an object in position relative to a bone hole. The method includes the steps of: (i) providing a knotless suture anchor construct comprising an anchor body extending between a first end and a second end, a filament having a first end and a second end, the filament woven through a plurality of passing locations along the anchor body such that the first end of the filament extends from the first end of the anchor body and the second end of the filament extends from the second end of the anchor body, a first passing portion in the filament between a first adjacent pair of the plurality of passing locations, and a second passing portion in the filament between a second adjacent pair of the plurality of passing locations; (ii) pulling the first passing portion to create a first loop; (iii) pulling the second passing portion to create a second loop; (iv) passing the second loop through the first loop; (v) inserting the knotless suture anchor construct into a bone hole; (vi) passing the first end of the filament through or around an object; (vii) passing the first end of the filament through the second loop; (viii) tensioning the first end of the filament and tractioning the second end of the filament, wherein tractioning the second end of the filament causes the second loop to decrease in size from a first diameter to a second diameter; and (ix) tractioning the second end of the filament farther, causing the second loop and the first end of the filament to pass through the first loop.

Embodiments of the knotless suture anchor construct described herein can include a fibrous construct anchor body portion (or fibrous, braided or woven fabric-type structure such as a flexible web), and a suture or filament portion having a first end and a second end. The anchor body can be hollow, cored, tubular or nontubular, and/or flat. The suture can pass through the anchor body in a number of ways (including woven, pass through a column, pierced through top and bottom, etc., as should be understood by a person of ordinary skill in the art in conjunction with a review of this disclosure). The anchor body can include a first state in which the anchor body is uncompressed and extends along the longitudinal axis of the suture when in an unfolded and pre-deployed condition; and a second state in which the flat anchor body is compressed and expanded in a direction perpendicular to longitudinal axis of the suture in a deployed condition to provide strong securing contact with the walls of a bone hole (as discussed herein). Stated differently, the anchor body portion is configured to take advantage of Poisson's ratio, which captures the following cause/effect relationship: compressing a material in a first direction causes the material to expand in direction perpendicular to the first direction (i.e., if compressed in the x-direction, the material will expand in the y-direction and/or z-direction), and stretching/lengthening a material in a first direction causes the material to contract in directions perpendicular to the first direction. Although, it is the anchor body portion that increases in width, thickness and/or diameter at deployment, it should be understood that the filament portion can also play a role in the deployment of the anchor even though the filament portion may remain free (in some embodiments) to slide, and non-slidable in others (at least at a particular position or point in use) in relation to the anchor body portion. The filament portion helps to position, align and support the anchor body portion upon deployment.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
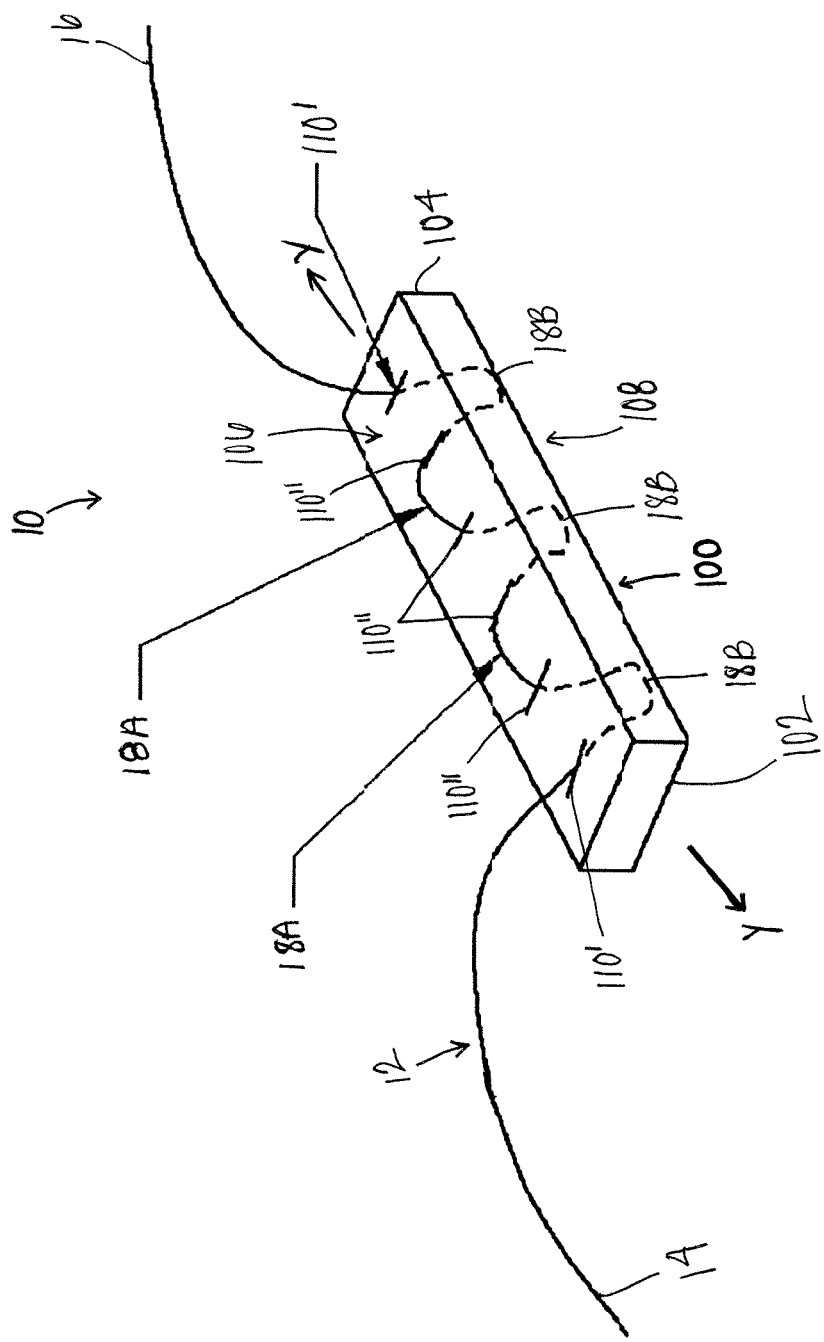
FIG. 1 is a top perspective view schematic representation of a knotless suture anchor construct, according to an embodiment.

Referring now to the figures, wherein like reference numerals refer to like parts throughout, FIG. 1 shows a top perspective view schematic representation of a knotless suture anchor construct 10, according to an embodiment. The knotless suture anchor construct 10 comprises an anchor body 100 with a filament 12 passing therethrough. In the depicted embodiment, the anchor body 100 is composed of braided suture and the filament 12 is a strand of suture. As also shown in FIG. 1, the anchor body 100 is rectangular, extending along a central longitudinal y-y axis between a first end 102 and a second end 104. Although a rectangular anchor body 100 is shown, the anchor body 100 may comprise any other known shape or geometry. The anchor body 100 additionally comprises a first side 106 and a second side 108, as shown in FIG. 1.

Still referring to FIG. 1, the filament 12 also comprises a first end 14 and a second end 16 and is woven through the anchor body 100 at a plurality of passing locations. In the depicted embodiment, the filament 12 is woven through the anchor body 100 at six passing locations. However, any number of passing locations can be used. Of the six passing locations shown in FIG. 1, there are two terminal passing locations 110' and four intermediary passing locations 110". One of the two terminal passing locations 110' is at the first end 102 of the anchor body 100 and the other of the two terminal passing locations 110' is at the second end 104 of the anchor body 100, as shown. The four intermediary passing locations 110" are along the anchor body 100 between the two terminal passing locations 110'.

The filament 12 is woven through the anchor body 100 such that the first end 14 of the filament 12 extends from the first end 102 of the anchor body 100 and the second end 16 of the filament 12 extends from the second end 104 of the anchor body 100. In addition, both the first and second ends 14, 16 of the filament 12 extend from the first side 106 of the anchor body 100 (but can each extend from the second side, or can separately extend from the first side and the second side respectively). In order to achieve the configuration shown in FIG. 1, the filament 12 is woven through the anchor body 100 such that there are one or more passing portions of the filament 12 on at least one of the first side 106 and the second side 108 of the anchor body 100. The passing portions are lengths of filament 12 between any two passing locations 110', 110". In the depicted embodiment, there are two passing portions 18A on the first side 106 of the anchor body 100 and three passing portions 18B on the second side 108 of the anchor body 100. However, there may be any number of passing portions 18A, 18B on either the first side 106 or the second side 108 of the anchor body 100 depending on the number of passing locations 110', 110" extending through the anchor body 100.

Figure 2:
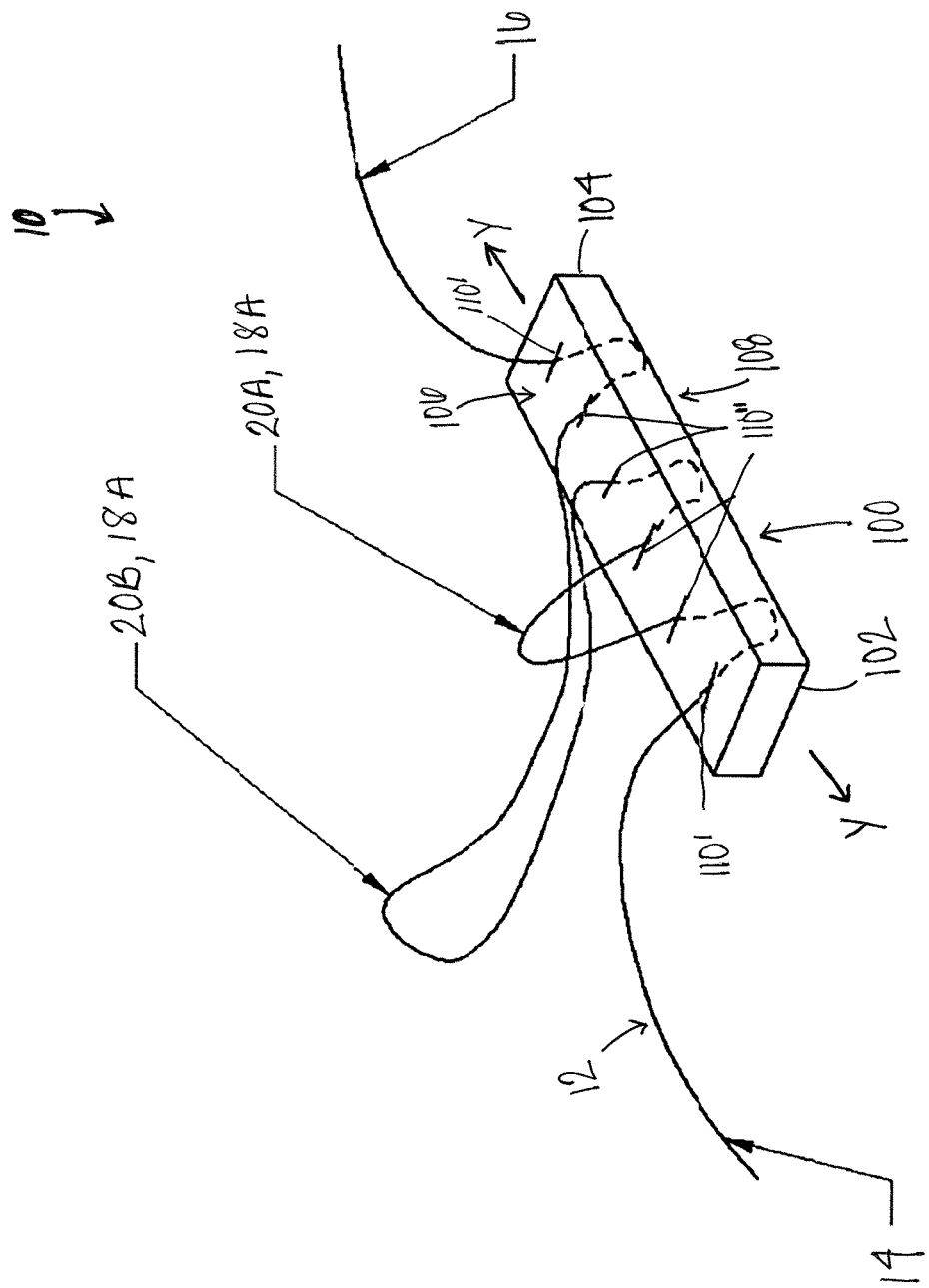
FIG. 2 is a top perspective view schematic representation of the knotless suture anchor construct in a pre-deployment configuration, according to an embodiment.

Turning now to FIG. 2, there is shown a top perspective view schematic representation of the knotless suture anchor construct 10 in a pre-deployment configuration, according to an embodiment. In the depicted embodiment, a first passing portion 18A of the anchor construct 10 in FIG. 1 has been passed through a second passing portion 18B of the anchor construct 10. In particular, slack is created in the first passing portion 18A by pulling the first passing portion 18A away from the first side 106 of the anchor body 100, creating a first loop 20A. Slack is also created in the second passing portion 18B by similarly pulling the second passing portion 18B away from the first side 106 of the anchor body 100, creating a second loop 20B. The second loop 20B is then passed through the first loop 20A, as shown in FIG. 2.

Figure 3:
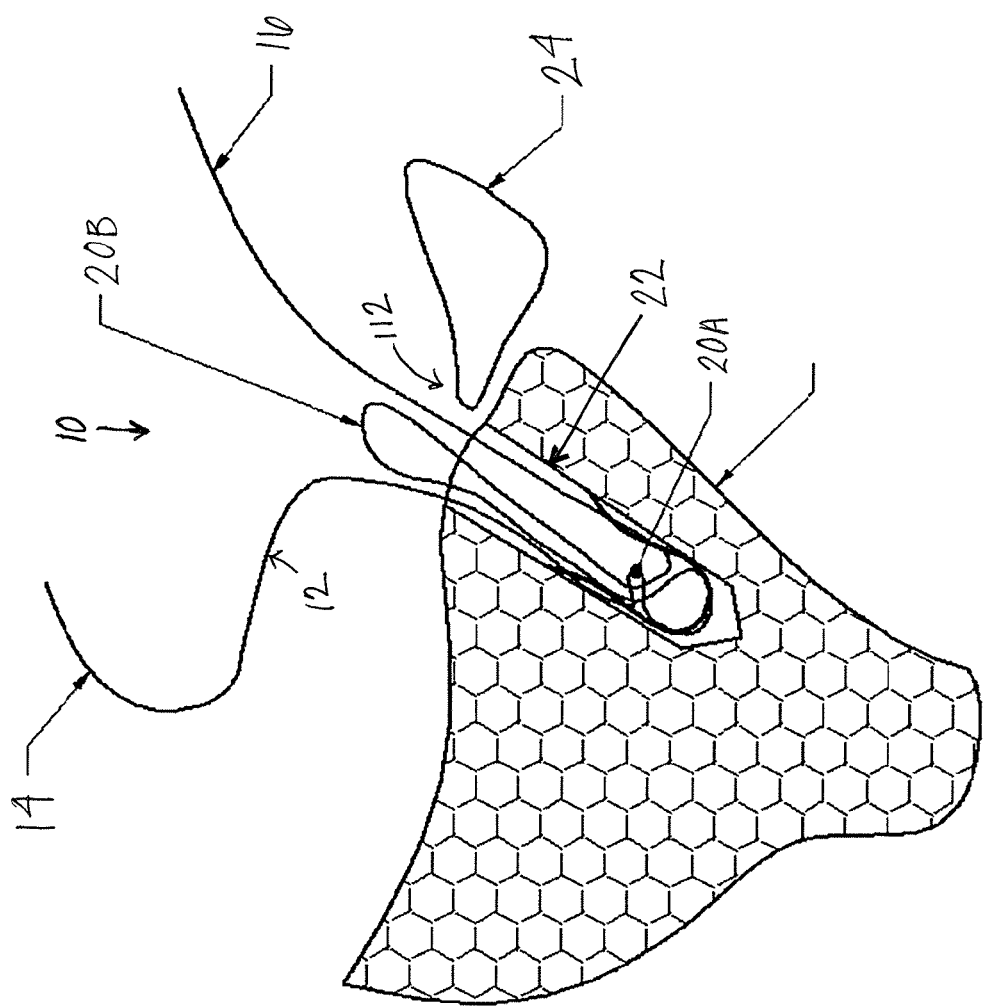
FIG. 3 is a side view schematic representation of the knotless suture anchor construct in a bone hole, according to an embodiment.

Referring now to FIGS. 3-6 there are shown side views schematic representations of the knotless suture anchor construct 10 at various stages of deployment, according to an embodiment. In the pre-deployment configuration shown in FIG. 2, the anchor construct 10 is inserted into a bone hole 22 near an object 24 to be repaired, such as a soft tissue, as shown in FIG. 3. The anchor construct 10, in the pre-deployment configuration, can be inserted into the bone hole 22 using a driver/inserter (not shown) or any other known device used to deploy suture anchors, e.g., U.S. Pat. No. 9,173,652 (as should be understood by a person of ordinary skill in the art in conjunction with a review of this disclosure). The anchor construct 10 can be loaded onto the driver and the driver pushes the anchor construct 10 into the bone hole 22, implanting it therein. The driver is then removed, leaving the anchor construct 10 within the bone hole 22, as shown in FIG. 3. The anchor construct 10 is within the bone hole 22 such that the first and second ends 14, 16 of the filament 12 extend on a first side 112 of the object 24 (e.g., soft tissue), as shown.

Figure 4:
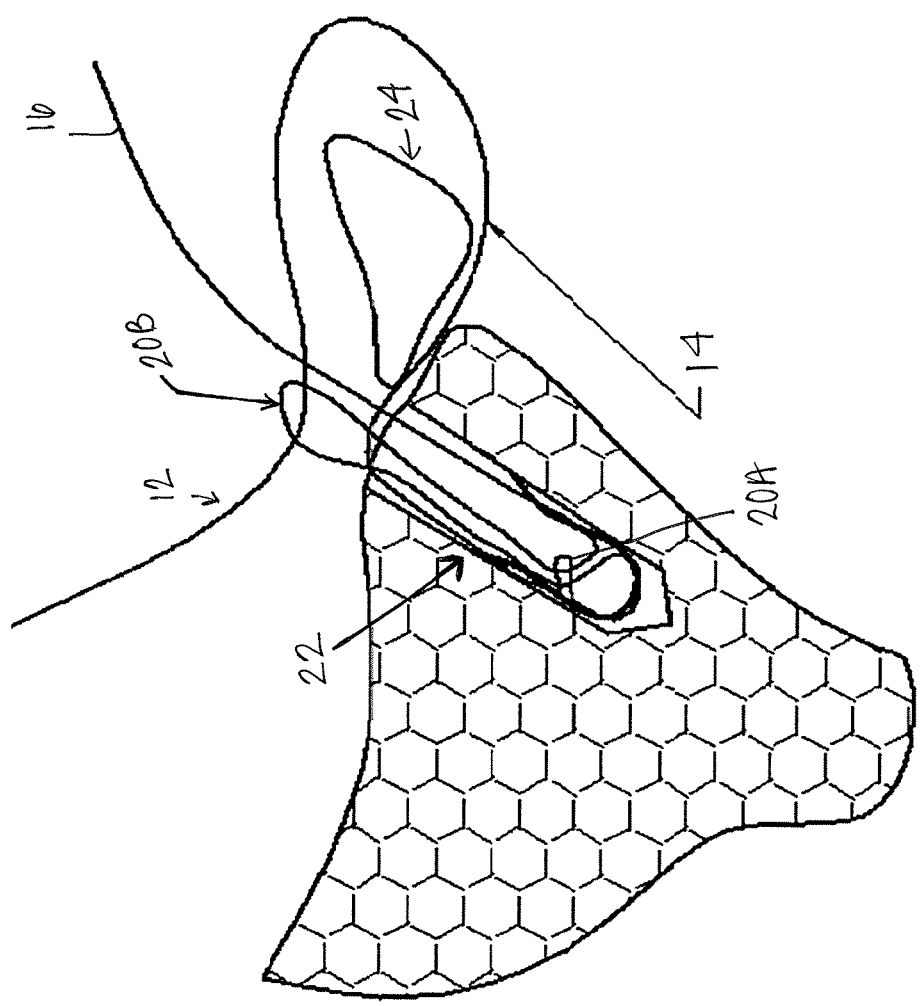
FIG. 4 is a side view schematic representation of the knotless suture anchor construct in a bone hole during deployment, according to an embodiment.
Figure 5:
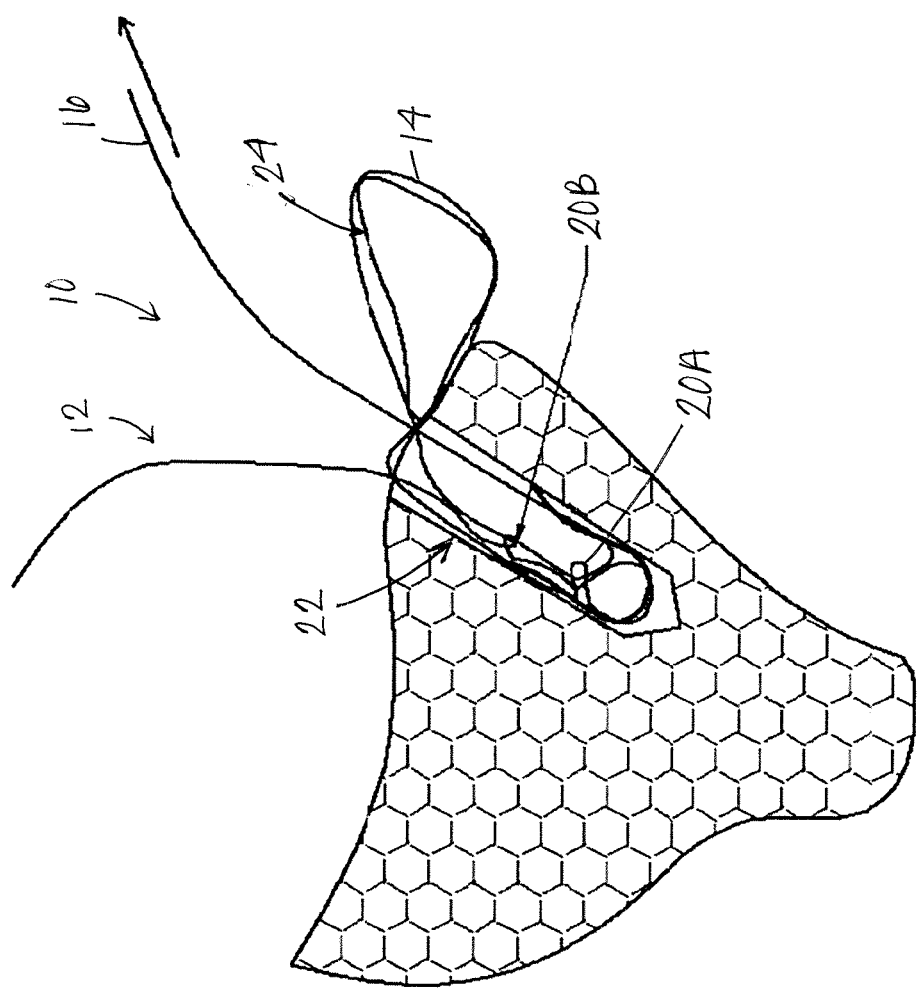
FIG. 5 is a side view schematic representation of the knotless suture anchor construct in a bone hole during deployment, according to an embodiment.

With the first and second ends 14, 16 of the filament 12 on the first side 112 of the object 24, the first end 14 of the filament 12 is passed through or around the object 24. After the first end 14 of the filament 12 is through or around the object 24, the first end 14 of the filament 12 is then passed through the second loop 20B, as shown in FIG. 4. Then, the second end 16 of the filament 12 is tractioned while tension is kept on the first end 14 of the filament 12. Traction on the second end 16 of the filament 12 draws the second loop 20B distally into the bone hole 22, as shown in FIG. 5. The second loop 20B is drawn into the bone hole 22 because the traction on the second end 16 of the filament 12 causes a decrease in the size of second loop 20B from a first diameter to a second smaller diameter.

Figure 6:
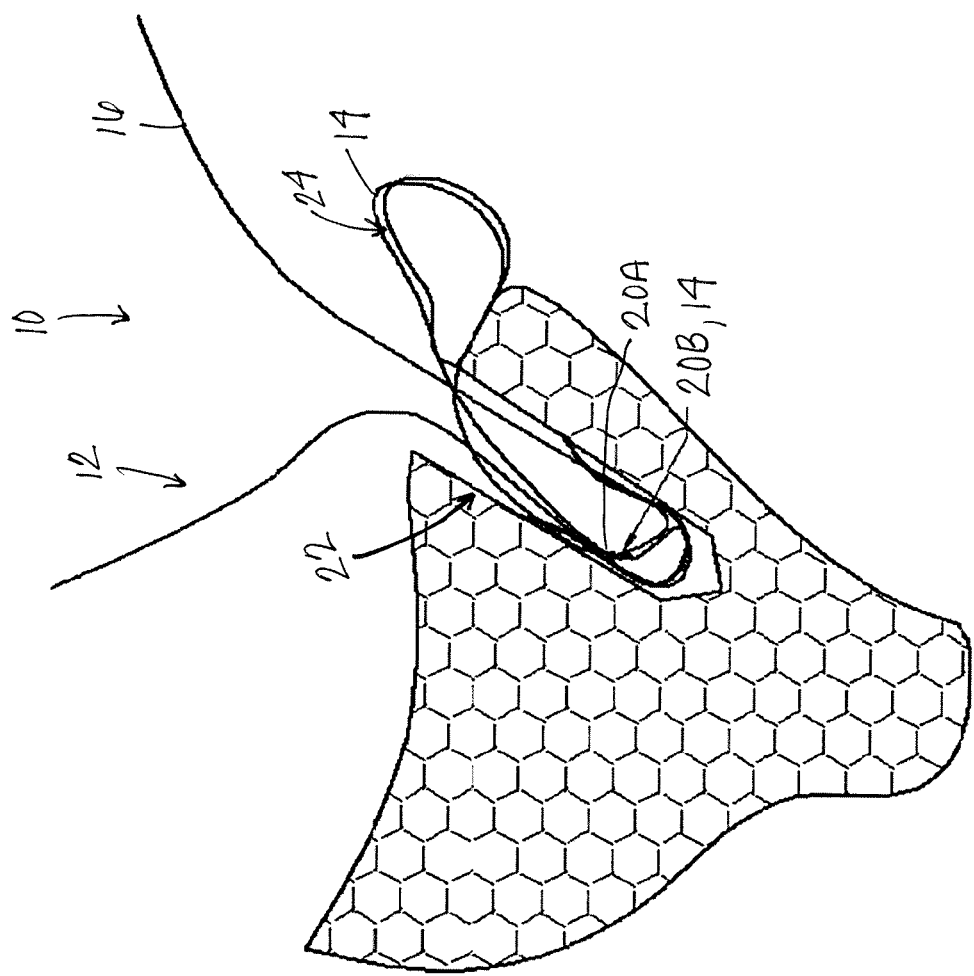
FIG. 6 is a side view schematic representation of the knotless suture anchor construct in the deployed configuration, according to an embodiment.

With the second loop 20B within the bone hole 22 (FIG. 5), traction is applied to the second end 16 of the filament 12. Traction on the second end 16 of the filament 12 pulls the second loop 20B and the first end 14 of the filament 12 through the first loop 20A, as shown in FIG. 6. When the second loop 20B and the first end 14 of the filament 12 pass through the first loop 20A, the anchor construct 10 is in the deployed configuration and the object 24 (e.g., soft tissue) is secured in relative position with respect to the bone hole 22. Filament 12 is reversibly movable during this process to allow for adjustment by pulling on first end 14 and no longer pulling on second end 16 (giving it some slack).

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A knotless suture anchor construct, comprising:
   an anchor body extending between a first end and a second end, the anchor body having a first side and a second side;
   a filament having a first end and a second end, the filament woven through a plurality of passing locations along the anchor body such that the first end of the filament extends from the first end of the anchor body and the second end of the filament extends from the second end of the anchor body;
   a first passing portion in the filament extending along the first side of the anchor body between and connected to a first adjacent pair of the plurality of passing locations;
   a second passing portion in the filament between a second adjacent pair of the plurality of passing locations; and
   wherein in a pre-deployment configuration, the first passing portion is pulled to form a first loop and the second passing portion is pulled to form a second loop, and the second loop extends through the first loop.

2. The construct of claim 1, wherein the first passing portion and the second passing portion are on the first side of the anchor body.

3. The construct of claim 1, wherein the plurality of passing locations is six passing locations.

4. The construct of claim 1, wherein in a deployed configuration, the first end of the filament is configured to extend through or around an object and through the second loop.

5. The construct of claim 4, wherein in the deployed configuration, the first end of the filament is tensioned and the second end of the filament is pulled such that the second loop decreases in size from a first diameter to a second diameter.

6. The construct of claim 5, wherein in the deployed configuration, the first end of the filament is tensioned and the second end of the filament is pulled such that second loop passes through the first loop.

7. The construct of claim 1, wherein the anchor body is composed of suture braid.

8. A method for securing an object in position relative to a bone hole, comprising the steps of:
   providing a knotless suture anchor construct comprising an anchor body extending between a first end and a second end, a filament having a first end and a second end, the filament woven through a plurality of passing locations along the anchor body such that the first end of the filament extends from the first end of the anchor body and the second end of the filament extends from the second end of the anchor body, a first passing portion in the filament between a first adjacent pair of the plurality of passing locations, and a second passing portion in the filament between a second adjacent pair of the plurality of passing locations; and
   pulling the first passing portion to create a first loop;
   pulling the second passing portion to create a second loop; and
   passing the second loop through the first loop.

9. The method of claim 8, further comprising the step of inserting the knotless suture anchor construct into a bone hole.

10. The method of claim 9, further comprising the step of passing the first end of the filament through or around an object.

11. The method of claim 10, further comprising the step of passing the first end of the filament through the second loop.

12. The method of claim 11, further comprising the step of tensioning the first end of the filament and tractioning the second end of the filament.

13. The method of claim 12, wherein tractioning the second end of the filament causes the second loop to decrease in size from a first diameter to a second diameter.

14. The method of claim 13, further comprising the step of tractioning the second end of the filament farther, causing the second loop and the first end of the filament to pass through the first loop.

15. The method of claim 10, wherein the object is soft tissue.

16. A knotless suture anchor construct, comprising:
   an anchor body extending between a first end and a second end, the anchor body having a first side and a second side;
   a filament having a first end and a second end, the filament woven through a plurality of passing locations along the anchor body such that the first end of the filament extends from the first end of the anchor body and the second end of the filament extends from the second end of the anchor body;
   a first passing portion in the filament between a first adjacent pair of the plurality of passing locations;
   a second passing portion in the filament extending along the first side of the anchor body between and connected to a second adjacent pair of the plurality of passing locations; and
   wherein in a pre-deployment configuration, the first passing portion is pulled to form a first loop and the second passing portion is pulled to form a second loop, and the second loop extends through the first loop.

17. The construct of claim 16, wherein the first passing portion and the second passing portion are on the first side of the anchor body.

18. The construct of claim 16, wherein the plurality of passing locations is six passing locations.

19. The construct of claim 16, wherein in a deployed configuration, the first end of the filament is configured to extend through or around an object and through the second loop.

20. The construct of claim 19, wherein in the deployed configuration, the first end of the filament is tensioned and the second end of the filament is pulled such that the second loop decreases in size from a first diameter to a second diameter.

21. The construct of claim 20, wherein in the deployed configuration, the first end of the filament is tensioned and the second end of the filament is pulled such that second loop passes through the first loop.

\* \* \* \* \*